United States Patent [19]
Faries, Jr. et al.

[11] Patent Number: 6,087,636
[45] Date of Patent: Jul. 11, 2000

[54] SURGICAL DRAPE AND STAND FOR USE IN HEATED THERMAL TREATMENT BASINS

[75] Inventors: Durward I. Faries, Jr., McLean, Va.;
Bruce R. Heymann, Silver Spring, Md.; Mark Licata, Richmond, Va.

[73] Assignee: O.R. Solutions, Inc., Chantilly, Va.

[21] Appl. No.: 08/807,095

[22] Filed: Feb. 27, 1997

[51] Int. Cl.[7] .............................. A61B 19/00; F27D 11/00; A61F 7/00

[52] U.S. Cl. .......................... 219/429; 219/430; 219/433; 219/439; 604/114

[58] Field of Search ...................... 219/385, 386, 219/214, 218, 429, 430, 432, 433, 438, 439; 4/545, 639; 604/113, 114; 220/577; 99/415, 418

[56] References Cited

U.S. PATENT DOCUMENTS

| | | | |
|---|---|---|---|
| 894,974 | 8/1908 | Nicodemus | 99/415 |
| 1,343,114 | 6/1920 | Colson | 99/418 |
| 1,453,054 | 4/1923 | Nordstrom | 99/418 |
| 2,101,487 | 12/1937 | Anderson | 99/418 |
| 2,244,193 | 6/1941 | Guyon et al. | 99/415 |
| 2,277,605 | 3/1942 | Paulitzsch | 219/439 |
| 2,364,537 | 12/1944 | Kerth | 99/418 |
| 2,778,921 | 1/1957 | Jepson | 219/439 |
| 3,155,260 | 11/1964 | Widener | 219/386 |
| 3,902,484 | 9/1975 | Winters . | |
| 4,393,659 | 7/1983 | Keyes et al. . | |
| 4,474,016 | 10/1984 | Winchell . | |
| 4,522,041 | 6/1985 | Menzel . | |
| 4,735,135 | 4/1988 | Walker | 99/415 |
| 4,782,835 | 11/1988 | Bernardini . | |
| 4,934,152 | 6/1990 | Templeton . | |
| 4,967,061 | 10/1990 | Weber et al. | 219/438 |
| 5,040,699 | 8/1991 | Gangemi . | |
| 5,042,455 | 8/1991 | Yue et al. . | |
| 5,129,033 | 7/1992 | Ferrara et al. | 219/438 |
| 5,163,299 | 11/1992 | Faries, Jr. et al. . | |
| 5,174,306 | 12/1992 | Marshall . | |
| 5,310,524 | 5/1994 | Campbell et al. . | |
| 5,331,820 | 7/1994 | Faries, Jr. et al. . | |
| 5,333,326 | 8/1994 | Faries, Jr. et al. . | |
| 5,363,746 | 11/1994 | Gordon . | |
| 5,374,813 | 12/1994 | Shipp . | |
| 5,383,476 | 1/1995 | Peimer et al. . | |
| 5,386,835 | 2/1995 | Elphick et al. . | |
| 5,400,267 | 3/1995 | Denen et al. . | |
| 5,400,616 | 3/1995 | Faries, Jr. et al. . | |
| 5,402,644 | 4/1995 | Faries, Jr. et al. . | |
| 5,429,801 | 7/1995 | Faries, Jr. et al. . | |
| 5,435,322 | 7/1995 | Marshall . | |

(List continued on next page.)

*Primary Examiner*—Joseph Pelham

[57] ABSTRACT

A stand is disposed in a heated thermal treatment system basin to support objects placed in the basin above the heated basin floor. The stand may be circular, rectangular or other shape to accommodate various shaped basins and prevent a surgical drape disposed in the basin and containing a heated sterile medium from puncturing. A substantially circular stand includes a substantially circular frame elevating a platform having a plurality of spokes reinforced by a plurality of concentric rings, while a substantially rectangular stand includes a substantially rectangular frame elevating a platform having a plurality of intersecting perpendicular rods to form a grid. Alternatively, the substantially circular stand may include a substantially circular platform having holes defined therein and legs extending downwardly from the platform to elevate the platform above the basin floor, while the substantially rectangular stand may include a substantially rectangular platform having holes defined therein with downwardly curved longitudinal ends to elevate the platform. The holes in the platforms, the spaces residing between the spokes and rings, and the spaces residing between the perpendicular rods, enable the stand to be submerged in the heated sterile medium and permit thermal energy from the basin to pass through the respective platforms and efficiently heat the sterile medium. The stand may be either a separate unit, or disposed integrally with the drape where the stand corresponds to the center of the basin and indicates the portions of the drape to be disposed in the basin.

31 Claims, 2 Drawing Sheets

U.S. PATENT DOCUMENTS

| | | |
|---|---|---|
| 5,443,082 | 8/1995 | Mewburn . |
| 5,449,892 | 9/1995 | Yamada . |
| 5,457,962 | 10/1995 | Faries, Jr. et al. . |
| 5,463,213 | 10/1995 | Honda . |
| 5,502,980 | 4/1996 | Faries, Jr. et al. . |
| 5,522,095 | 6/1996 | Faries, Jr. et al. . |
| 5,524,643 | 6/1996 | Faries, Jr. et al. . |
| 5,539,185 | 7/1996 | Polster ................................. 219/439 |
| 5,551,240 | 9/1996 | Faries, Jr. et al. . |
| 5,615,423 | 4/1997 | Faries, Jr. et al. . |
| 5,653,938 | 8/1997 | Faries, Jr. et al. . |

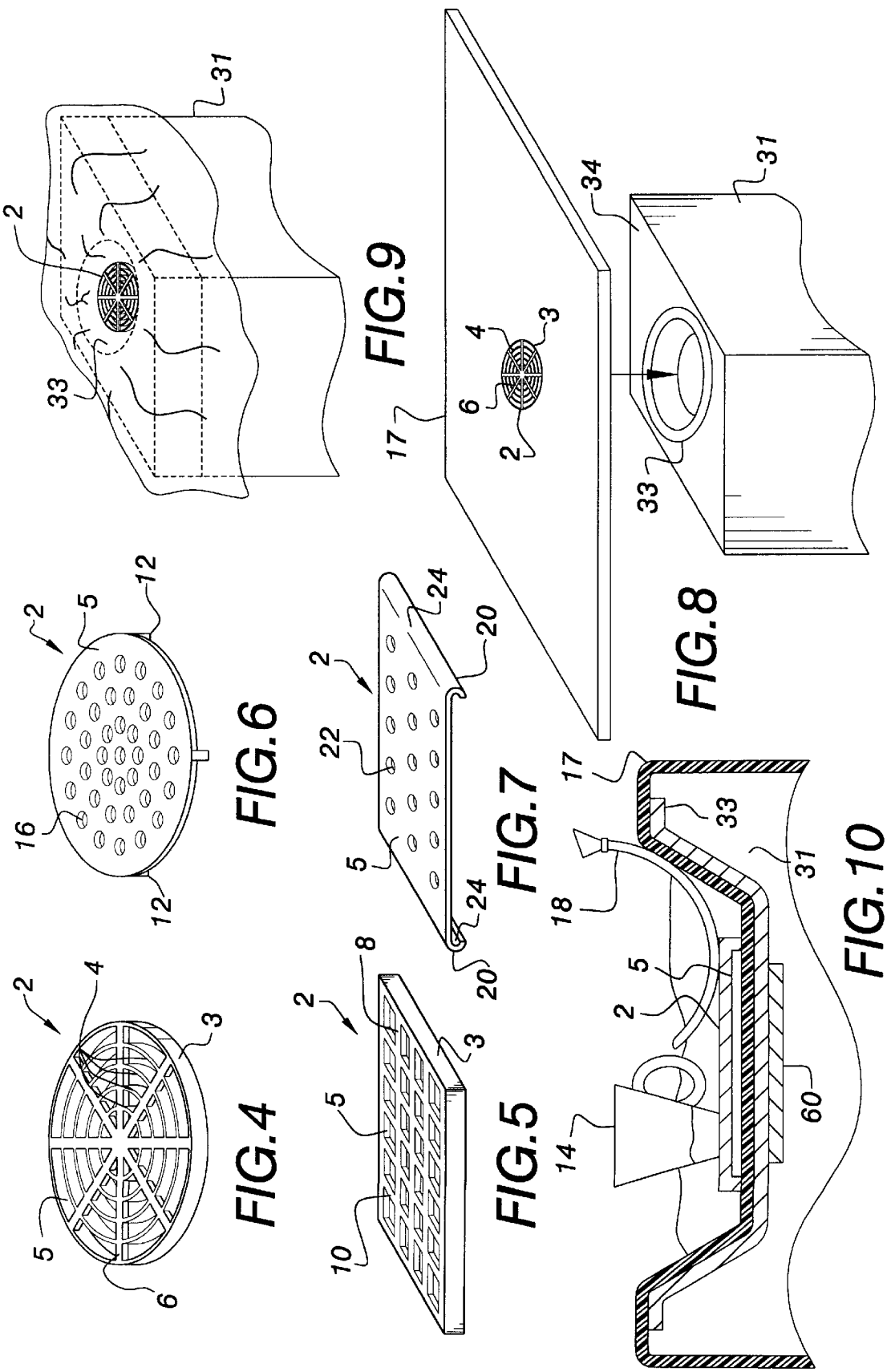

SURGICAL DRAPE AND STAND FOR USE IN HEATED THERMAL TREATMENT BASINS

BACKGROUND OF THE INVENTION

1. Technical Field

The present invention pertains to improvements in methods and apparatus for thermally treating surgically sterile liquid. In particular, the invention is an improvement of the methods and apparatus disclosed in U.S. Pat. No. 4,393,659 (Keyes et al), U.S. Pat. No. 4,934,152 (Templeton), U.S. Pat. No. 5,333,326 (Faries, Jr. et al). The disclosures in those patents are expressly incorporated herein in their entireties by this reference.

2. Discussion of the Prior Art

The Keyes et al patent discloses a surgical slush producing system having a cabinet with a heat transfer basin at its top surface. A refrigeration mechanism in the cabinet takes the form of a closed refrigeration loop including: an evaporator in heat exchange relation to the exterior of the heat transfer basin; a compressor; a condenser; and a refrigeration expansion control, all located within the cabinet. A separate product basin is configured to be removably received in the heat transfer basin. Spacers, in the form of short cylindrical stubs or buttons are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile sheet of material, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency in the product basin.

As noted in the Templeton patent, the above-described system has a number of disadvantages. In particular, the separate product basin must be removed and resterilized after each use. Additionally, the glycol or other thermal transfer medium is typically highly flammable or toxic and, in any event, complicates the procedure. The Templeton patent discloses a solution to these problems by constructing an entirely new apparatus whereby the product basin is eliminated in favor of a sterilized drape impervious to the sterile surgical liquid, the drape being made to conform to the basin and directly receive the sterile liquid. Congealed liquid is scraped off the sides of the conformed drape receptacle to form the desired slush.

In addition, Templeton also provides an electrical heater disposed at the bottom of the basin to convert the sterile slush to warmed liquid, or heat additional sterile liquid added to the basin. Templeton describes the need for such warm sterile liquid as occurring after a surgical procedure is completed to facilitate raising the body cavity of a surgery patient back to its normal temperature by contact with the warm liquid. However, there are a number of instances during a surgical procedure when it is desirable to have simultaneous access to both the sterile warm liquid and the sterile surgical slush. For example, if the surgical slush is not of the desired consistency (e.g., too thick), the availability of warm sterile liquid to be added to the slush permits rapid adjustability of the slush consistency. Likewise, maintaining instruments at or near body temperature during surgery is a desirable feature permitted by warm sterile liquid. Of course, if the warm sterile liquid is simultaneously available with the surgical slush, there is no need to wait for the slush to melt at the end of the surgical procedure. Finally, the simultaneous provision of slush and warm liquid permits the two to be comprised of different compounds as is sometimes necessary for various surgical procedures.

In response to the foregoing problems, the Faries Jr., et al U.S. Pat. No. (5,333,326) provides a thermal treatment system having a basin for containing warm surgical liquid placed adjacent a surgical slush basin of the type for example disclosed in the Templeton patent. The warming basin may be a separate unit secured to the pre-existing surgical slush unit, or may be constructed as part of an integral cabinet for the warming and cooling basins. A large surgical drape covers both of the basins and contains the warm liquid and the slush in a sterile manner. Alternatively, the thermal treatment system may include only the warming basin utilizing a drape to cover the basin and contain warm surgical liquid in a sterile manner. Generally, users of the aforementioned systems utilize the liquid in the warming basin to heat objects (e.g., medical instruments, containers) placed in the basin. However, placement of objects in the basin may puncture the drape in several different ways. For example, objects placed in the warming basin may trap air between the object base and drape material. The trapped air typically expands beneath the object when heated and expels the sterile liquid from beneath the object, thereby leaving the drape to absorb additional thermal energy from the basin at locations where liquid has been expelled. The additional thermal energy causes the drape to overheat, melt, and stick to the warming basin, thereby forming holes. Further, the drape material may soften significantly when exposed to the heated basin floor, thereby allowing normally safe (i.e., dull or blunt) objects to puncture the material (e.g., blunt plastic syringe tips and blunt tipped hemostats). Moreover, lack of sufficient liquid in the basin due to user error or evaporation tends to increase the amount of thermal energy absorbed by the drape, thereby causing portions of the drape to overheat forming hot spots and pinholes.

OBJECTS AND SUMMARY OF THE INVENTION

Accordingly, it is an object of the present invention to prevent puncturing of a surgical drape disposed in a heated thermal treatment system basin when objects (e.g., medical instruments, containers) are placed in the basin.

It is another object of the present invention to prevent puncturing of a surgical drape disposed in a heated thermal treatment system basin by supporting objects placed in the basin above the heated basin floor.

Yet another object of the present invention is to prevent puncturing of a surgical drape disposed in a heated thermal treatment system basin by supporting objects placed in the basin above the heated basin floor via a stand disposed in the basin.

Still another object of the present invention is to prevent puncturing of a surgical drape disposed in a heated thermal treatment system basin by supporting objects placed in the basin above the heated basin floor via a stand disposed integral with the drape.

A further object of the present invention is to indicate which portions of a surgical drape are to be disposed in a heated thermal treatment system basin by disposing a stand on the drape at a location corresponding to, and for designating, the approximate bottom center of the basin.

The aforesaid objects are achieved individually and in combination, and it is not intended that the present invention be construed as requiring two or more of the objects to be combined unless expressly required by the claims attached hereto.

According to the present invention, an elevated platform or stand is disposed in a heated thermal treatment system basin to support objects (e.g., medical instruments, containers, etc.) placed in the basin above the heated basin floor. The stand is placed on a surgical drape disposed within the basin and serving as a container for sterile liquid wherein the stand supports the objects to prevent portions of the drape coincident heated portions of the basin floor from overheating and puncturing. The stand may be either a separate unit, or disposed integrally with the drape. The stand includes a platform that may be of any shape to permit the platform to fit in horizontal orientation in the particular basin in which the stand is disposed (e.g., circular, polygonal, elliptical). The platform is oriented horizontally in the basin to elevate objects via support from either a frame or a plurality of legs.

By way of example, the platform may be substantially circular and disposed on, and elevated by, a substantially circular frame. The circular platform is preferably formed by a plurality of radial spokes, originating at the frame and extending toward the center of the area bounded by the frame, and a series of substantially equidistant concentric rings extending radially outward from the center and secured to the spokes to reinforce and strengthen the platform to support the objects. The platform may alternatively be substantially rectangular and disposed on, and elevated by, a substantially rectangular frame where the rectangular platform is formed by the intersection of a plurality of perpendicular bars originating from respective longitudinal and transverse sides of the frame. The intersecting perpendicular bars form a mesh grid to support the objects. Spaces residing in the circular platform between the spokes and rings, and in the rectangular platform between the longitudinal and transverse bars, maintain the stand in a submerged state in the liquid filled basin while allowing thermal energy from the basin to pass through respective platforms and efficiently heat the liquid.

Alternatively, the stand may include a substantially circular platform having a plurality of legs disposed at its circumferential edges to elevate the platform and support objects above the basin floor. Further, a stand having a substantially rectangular platform with each of its longitudinal ends curved downwardly approximately one-hundred eighty degrees to elevate the platform may be utilized to support objects above the basin floor. A plurality of openings are defined through the circular and rectangular platforms such that the stand maintains a submerged state in the liquid filled basin while allowing thermal energy in the basin to pass through respective platforms and efficiently heat the liquid.

When disposed integral with the drape, the stand is positioned at a location on the drape corresponding to the approximate center of the basin. The stand functions to indicate the portions of the drape that are to be disposed in the basin with the stand positioned at the approximate center of the basin floor. Any of the above described stands may be disposed on the drape to support objects above the basin floor and prevent the drape from puncturing in substantially the same manner described above for the respective stand embodiments.

The above and still further objects, features and advantages of the present invention will become apparent upon consideration of the following detailed description of the specific embodiments thereof, particularly when taken in conjunction with the accompanying drawings wherein like reference numerals in the various figures designate like components.

BRIEF DESCRIPTION OF THE DRAWINGS

FIG. 4 is a view in perspective of a stand having a substantially circular platform elevated by a frame for supporting objects in a substantially circular heated thermal treatment system basin according to the present invention.

FIG. 5 is a view in perspective of a stand having a substantially rectangular platform elevated by a frame for supporting objects in a substantially rectangular heated thermal treatment system basin according to the present invention.

FIG. 6 is a view in perspective of a stand having a substantially circular platform elevated by legs to support objects in a substantially circular heated thermal treatment system basin according to the present invention.

FIG. 7 is a view in perspective of a stand having a substantially rectangular platform elevated by curved longitudinal ends for supporting objects in a substantially rectangular heated thermal treatment system basin.

FIG. 8 is an exploded view of a surgical drape including a stand integral with the drape for supporting objects in a heated thermal treatment system basin according to the present invention.

FIG. 9 is a view in perspective of the drape and stand disposed in the heated thermal treatment system basin of FIG. 8.

FIG. 10 is a view in elevation and partial section of a drape and stand supporting objects in a heated thermal treatment system basin according to the present invention.

DESCRIPTION OF THE PREFERRED EMBODIMENTS

Figure 1:
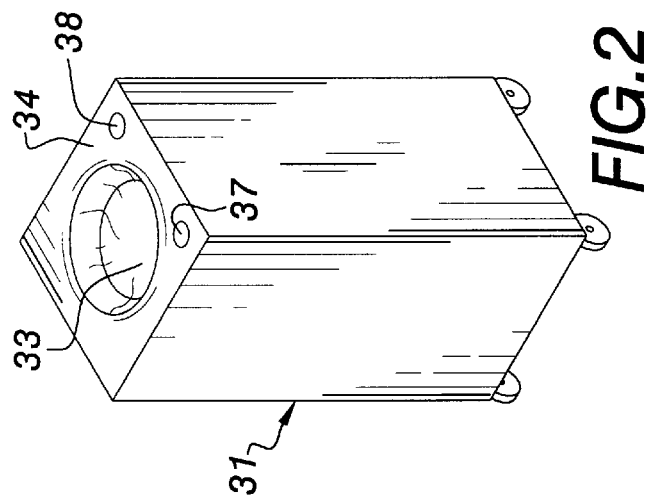
FIG. 1 is a view in perspective of a thermal treatment system containing a substantially rectangular warming basin employed by the present invention.
Figure 2:
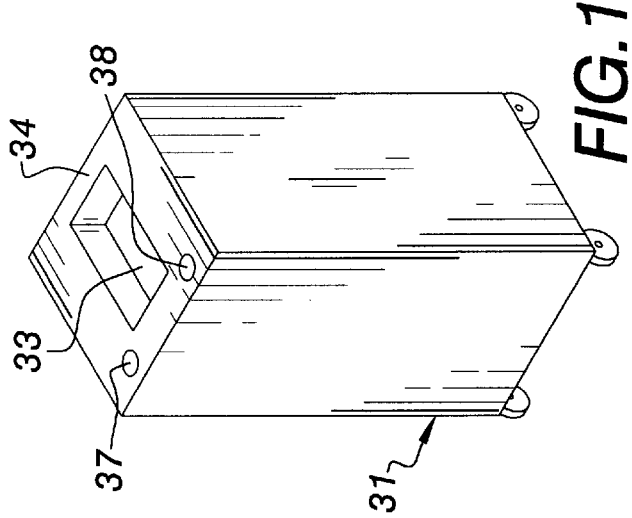
FIG. 2 is a view in perspective of a thermal treatment system containing a substantially circular warming basin employed by the present invention.

Referring to FIGS. 1–2 of the accompanying drawings, a typical thermal treatment system for heating a sterile medium (i.e., liquid) employed by the present invention includes a cabinet or housing 31 and a warming basin 33 recessed into the top surface 34 of cabinet 31. Basin 33 may be any shape, however, by way of example only, the basin is illustrated as being either substantially rectangular (FIG. 1) or substantially circular (FIG. 2). A heater power switch 37 and a temperature controller/indicator 38 are provided on top surface 34 adjacent the warming basin. It is to be understood that the thermal treatment system described above may have various configurations and include a plurality of basins warming and/or cooling a sterile medium. An example of such a system is disclosed in the aforementioned Faries, Jr. et al, (U.S. Pat. No. 5,333,326) patent.

Figure 3:
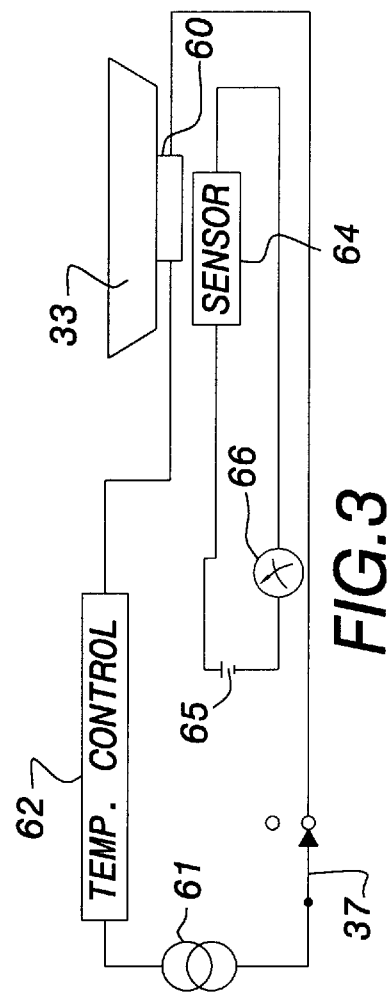
FIG. 3 is an electrical schematic diagram of the heating unit employed in the thermal treatment systems of FIGS. 1, 2.

The manner of heating sterile liquid in a warming basin (e.g., warming basin 33 of FIGS. 1, 2) is illustrated schematically in FIG. 3. Specifically, an electrical circuit includes a power source 61 connected in series with a temperature control unit 62, a heater element or pad 60, and power control switch 37. Heater 60 is typically a thin wafer-like member disposed along the bottom surface of heating basin 33, secured to the basin by a suitable pressure sensitive adhesive having efficient heat transfer characteristics. Heater 60 has smaller dimensions than the basin bottom and is disposed at the approximate center of the bottom surface of the basin. The heater, for example, may be of the type described in the aforementioned Templeton patent. Temperature control unit 62 includes a device for adjusting current passing through the heating element 60 so as to permit selective adjustment of the heat applied to the liquid in basin 33. The power switch 37 permits selective application and removal of current flow with respect to heater 60.

A temperature sensor 64 is disposed adjacent basin 33 to sense the temperature of the liquid therein. Sensor 64 is connected in series with a voltage source 65 and an indicator 66. Voltage source 65 and power source 61 may be the same source, or the voltage for one may be derived from the other. Indicator 66 measures the current through temperature sensor 64, that current being proportional to the sensed temperature. Indicator 66 and temperature controller 62 may correspond, for example, to the temperature controller/indicator 38 described above. For further details on the operation of the heating unit, reference is made to the Faries, Jr. et al (U.S. Pat. No. 5,333,326) and other abovementioned patents.

A sterile drape suitable for covering the top surface of either system described above is made of a material that is impervious to the heated liquid, and is sufficiently soft and flexible to conform to the walls of basin 33 and form a drape receptacle. The thickness of the drape is preferably minimized to render thermal transfer therethrough most efficient, yet the thickness is sufficient to resist tearing and puncturing of the drape during normal use. Typically, by way of example only, a drape is made of materials commonly used in hospitals for surgical drapes and has a thickness in the range of 4.5 to 6.0 mils. The drape may also be made of polyurethane film as disclosed for the drape in the aforementioned Templeton patent. The drape is designed to be disposable after a single use and is provided presterilized and prepackaged in a leak-proof plastic bag or other sealed container to preserve the sterile nature of the drape during storage.

The drape is typically placed over the system and covers the top surface and hangs down the sides of the system cabinet while a portion of the drape is pushed down into, and conforms to, the basin to form a drape receptacle for containing heated liquid. Generally, objects (e.g., medical instruments, containers) may be warmed in the basin by placing the objects in heated liquid contained by the drape receptacle. However, placement of objects in the basin may trap air between the object base and the drape such that the trapped air expands when heated and expels liquid from the proximity of the drape. Consequently, the drape absorbs additional thermal energy from the basin coincident locations where the liquid has been expelled. The absorption of additional thermal energy may cause the drape to overheat, melt and stick to the basin, thereby creating a pinhole. Further, additional absorption of thermal energy by the drape, and hence puncturing, may occur due to lack of sufficient liquid in the basin via evaporation or user error. Moreover, the drape may soften when exposed to the heated area of the basin, thereby becoming susceptible to punctures from normally blunt, dull or "safe" objects (e.g., blunt plastic syringe tips and blunt tipped hemostats). An elevated platform or stand for supporting the objects in the heated basin and preventing heated portions of the drape coincident the heating element from puncturing is illustrated in FIGS. 4–7. Specifically, stands 2 are separate stand-alone units and are typically placed in a thermal treatment system basin adjacent the basin floor and within a drape receptacle containing heated liquid. Stands 2 may include platforms 5 of any shape (e.g., circular, polygonal, elliptical) to match the shape of the particular basin in which the stand is disposed. By way of example, and for purposes of illustration only, platform 5 is either substantially rectangular or substantially circular. Stands 2 may be constructed of any material that is sufficiently rigid and can withstand temperatures of at least one-hundred sixty degrees Fahrenheit. Preferably, stands 2 are made of a high density polyethylene, ABS thermoplastic or a polypropolyene material.

Referring to FIG. 4, stand 2 includes a frame 3, and a substantially circular elevated platform 5 for optimal use in a substantially circular basin. Frame 3 is a circular ring oriented horizontally for disposal in a thermal treatment system basin. The frame may be implemented by a rod of suitable cross-sectional shape (e.g., circular, polygonal, elliptical) or preferably, a thin band of substantially rectangular cross-section formed in the shape of a ring. Frame 3 has a height of, or elevates platform 5 above the basin floor to, approximately one-sixth the height of the basin. The diameter of frame 3 is slightly less than the diameter of the basin, but greater than the dimensions of heater 60 (FIG. 3) disposed beneath the basin floor such that the frame may be positioned in the basin with its edges coincident non-heated portions of the basin floor as described below. Platform 5 is supported by, and disposed at the top of, frame 3 and includes a series of rods or spokes 6 extending from the circumferential edges of the frame toward the center of the area bounded by frame. Spokes 6 are spaced substantially equidistant from each other and may extend along either the radii of frame 3 and terminate at the center of the frame, or extend diametrically across frame 3 with the spokes stacked or interleaved at an intersection point located at the approximate center of the frame. The spokes may be implemented by bars or rods of suitable cross-sectional shapes (e.g., polygonal, elliptical, circular), or preferably, substantially flat bars of generally rectangular cross-sections having thicknesses less than the height of the frame so as not to contact the basin floor. A plurality of concentric substantially circular rings 4 extend radially outward from the frame center and intersect, and are secured by, spokes 6. The rings are preferably equally spaced with each successive ring having a successively increasing diameter. Rings 4 are substantially similar to frame 3 except that the diameters and height of the rings are less than the respective diameter and height of the frame. Rings 4 reinforce spokes 6 and strengthen the platform structure to support the weight of objects. Concentric rings 4 may be either partitioned into segments and disposed between adjacent spokes, or disposed above or beneath the spokes to accommodate the intersection of the spokes and rings. Alternatively, spokes 6 may be partitioned into segments and disposed between rings 4 to accommodate the intersection of the spokes and rings. The spoke and ring arrangement of platform 5 is generally similar in appearance to a circular barbeque grill or burner of a conventional stove.

Stand 2 is disposed in thermal treatment system warming basin 33 (FIG. 2) having a drape disposed in the basin forming a drape receptacle to contain heated liquid. Stand 2 is oriented horizontally and immersed in the liquid adjacent the basin floor such that frame 3 rests on the drape coincident non-heated portions of the basin (i.e., beyond the perimeter of the heating element). Spaces residing in platform 5 between rings 4 and spokes 6 permit liquid to exist and flow through the platform, thereby maintaining stand 2 in a submerged state and allowing thermal energy from the basin to pass through the platform and efficiently heat the liquid. Objects disposed in the basin are placed on platform 5 wherein the platform elevates the objects above heated portions of the basin floor that are in direct contact with the heater. The space between the objects and the basin floor prevents air from becoming trapped between the object base and the drape while maintaining liquid in thermal relation with the drape such that the drape absorbs the proper amount of thermal energy and does not puncture as described above. Further, stand 2 separates the objects from the drape such that even safe (i.e., dull or blunt) objects are prevented from contacting and puncturing vulnerable heated portions of the drape.

A similar stand for use in a substantially rectangular basin is illustrated in FIG. 5. Specifically, stand 2 includes a frame 3 and a substantially rectangular elevated platform 5. Frame 3 is substantially rectangular and is oriented substantially horizontally for disposal in the basin. The frame may be implemented by a rod of varying cross-sectional shape (e.g., circular, polygonal, elliptical) or, preferably, a thin band of substantially rectangular cross-section formed in substantially the shape of a rectangle. Frame 3 has a height of, or elevates platform 5 above the basin floor for, approximately one-sixth the height of the basin. The dimensions of frame 3 are slightly less than the dimensions of the basin, but greater than the dimensions of heater 60 (FIG. 3) disposed beneath the basin floor such that the frame may be positioned in the basin with its edges coincident non-heated portions of the basin floor as described below. Platform 5 is supported by, and disposed at the top of, frame 3 and includes a plurality of longitudinal and transverse bars or rods 8, 10. Longitudinal rods 8 extend along substantially the entire length of the longitudinal axes of the frame, while transverse rods 10 extend along substantially the entire length of the transverse axes of the frame generally perpendicular to the longitudinal rods. Rods 8, 10 may be implemented by bars or rods having suitable cross-sectional shapes (e.g., polygonal, circular, elliptical) or, preferably, by substantially flat bars having a generally rectangular cross-section. Each longitudinal rod 8 extends from a longitudinal side of frame 3 and intersects every transverse rod 10 until reaching the opposing longitudinal side of the frame. Similarly, each transverse rod 10 extends from a transverse side of frame 3 and intersects every longitudinal rod 8 until reaching the opposing transverse side of the frame. The intersecting longitudinal and transverse rods 8, 10 form a mesh grid to enable the platform to support objects. The thickness or diameter of the longitudinal and transverse rods is substantially less than the height of frame 3 to prevent the rods from contacting the drape. The longitudinal and transverse rods 8, 10 may be interleaved such that the rods either pass over or under each other at the intersection points. Alternatively, one set of rods may be partitioned into a plurality of short segments and disposed between the other set of rods to accommodate both sets of rods at the intersection points (i.e., a set of full length rods extends through a set of partitioned rods between the short segments). The longitudinal and transverse rod arrangement of platform 5 is similar in appearance to a grid or grill.

Stand 2 is placed in basin 33 (FIG. 1) having a drape disposed therein to form a drape receptacle to contain heated liquid. The stand is oriented horizontally and immersed in the liquid adjacent the basin floor such that frame 3 rests on the drape at basin locations that are not directly heated portions of the basin (i.e., beyond the perimeter of the heating element). Spaces residing in platform 5 between longitudinal and transverse rods 8, 10 permit liquid to exist and flow through the platform, thereby maintaining stand 2 in a submerged state and allowing thermal energy from the basin to pass through the platform and efficiently heat the liquid. Objects disposed in the basin are placed on platform 5 wherein the platform elevates the objects above heated portions of the basin floor. The space between the objects and the basin floor allows for proper absorption of thermal energy by the drape while separating the objects from vulnerable heated portions of the drape to prevent the drape from puncturing in substantially the same manner described above.

An alternative embodiment of stand 2 utilizing legs to support a substantially circular platform is illustrated in FIG. 6. Specifically, stand 2 includes a plurality of legs 12, and a substantially circular elevated platform 5 for use in a substantially circular basin. Platform 5 is oriented substantially horizontally for disposal in the basin with legs 12 extending downwardly from the platform substantially similar in appearance to a small table. Platform 5 is substantially similar to a circular disk and may have any thickness sufficient to enable the platform to support the weight of objects placed in the basin. Legs 12 are disposed about, and extend downwardly from, the circumferential edges of platform 5 for elevating the platform for approximately one-sixth the height of the basin. Legs 12 may be straight, curved or include a slight bend and may be implemented by rods having various cross-sectional shapes (i.e., circular, polygonal, elliptical). Further, numerous types of bases for maintaining legs 12 in an erect posture may be disposed at the distal ends of the legs. The diameter of platform 5 is less than the diameter of the basin, but greater than the diameter of heater 60 (FIG. 3) disposed beneath the basin floor such that the legs may be positioned in the basin coincident portions of the basin floor that are not directly heated as described below. A plurality of substantially circular openings or holes 16, substantially similar in size, are defined through platform 5 to enable stand 2 to maintain a submerged state within the liquid filled basin and allow thermal energy from the basin to pass through the platform and efficiently heat the liquid. The number, size, and arrangement of holes 16 may be any number, size and/or arrangement capable of maintaining stand 2 in a submerged state and passing thermal energy to the liquid. The stand is disposed in basin 33 (FIG. 2) including a drape disposed in the basin forming a drape receptacle to contain heated liquid. Stand 2 is oriented horizontally and is immersed in the heated-liquid adjacent the basin floor such that legs 12 rest on the drape coincident portions of the basin that are not directly heated (e.g., beyond the perimeter of the heating element). Holes 16 permit liquid to flow through the platform, thereby maintaining stand 2 in a submerged state and allowing thermal energy from the basin to pass through the platform and efficiently heat the liquid. Objects disposed in the basin are placed on platform 5 wherein the platform elevates the objects above heated portions of the basin floor coincident the heater. The space between the objects and the basin floor allows for proper absorption of thermal energy by the drape while separating the objects from vulnerable heated portions of the drape to prevent the drape from puncturing in substantially the same manner described above.

Similarly, an alternative stand for use in a generally rectangular basin is illustrated in FIG. 7. Specifically, stand 2 includes a substantially rectangular platform 5 having curved longitudinal ends 20 for elevating the platform, and is substantially similar in appearance to certain modem desk or table designs. Platform 5 may be of any thickness capable of supporting objects placed in the basin and enabling the platform to be sufficiently flexible to form the curved longitudinal ends. Platform 5 is oriented substantially horizontally for disposal in the basin, with each longitudinal end 20 curved downwardly from the platform forming an approximate one-hundred eighty degree arc 24. Arcs 24 function as legs to support and elevate platform 5 above the basin floor for approximately one-sixth the height of the basin. The dimensions of platform 5 are slightly less than the dimensions of the basin, but greater than the dimensions of heater 60 (FIG. 3) disposed beneath the basin floor such that the bottom edges of arcs 24 may be positioned in the basin coincident non-heated portions of the basin floor as described below. Substantially circular holes or openings 22 are defined through platform 5 to maintain stand 2 in a submerged state within the liquid filled basin and allow thermal energy from the basin to pass through the platform and efficiently heat the liquid. Holes 22 are substantially similar in size and are arranged in a series of rows and columns, but any arrangement, size or number of holes capable of maintaining the submerged state and passing thermal energy to the liquid may be used. Stand 2 is disposed in basin 33 (FIG. 1) including a drape disposed in the basin forming a drape receptacle to contain heated liquid. The stand is oriented horizontally and immersed in the liquid adjacent the basin floor such that curved longitudinal ends 20 rest on the drape coincident non-heated portions of the basin (i.e., beyond the perimeter of the heating element). Holes 22 permit liquid to flow through platform 5, thereby maintaining stand 2 in a submerged state and allowing thermal energy from the basin to pass through the platform and efficiently heat the liquid. Objects disposed in the basin are placed on platform 5, wherein the platform elevates the objects above heated portions of the basin floor coincident the heater. The space between the objects and basin floor allows for proper absorption of thermal energy by the drape while separating the objects from vulnerable heated portions of the drape to prevent the drape from puncturing in substantially the same manner described above.

The stand may be a separate unit as described above, or alternatively be disposed on, and integral with, a surgical drape disposed in the basin as illustrated in FIGS. 8–9. Specifically, drape 17 is a surgical drape substantially similar to the drape described above. By way of example only, stand 2 is substantially similar to the stand having a substantially circular platform and frame described above, however, it is to be understood that any of the above-described stands may be disposed integral with the drape and function to elevate objects in substantially the same manner described above for the respective stand embodiments. Stand 2 may be attached to drape 17 by use of ultrasonic energy, heat welding, solvents, adhesives, RF welding techniques or any other appropriate or conventional attachment process. The stand is preferably disposed at the approximate center of drape 17, and may also be utilized as an indicator for directing placement of the drape over thermal treatment system cabinet 31. In particular, stand 2 is disposed on drape 17 such that the stand corresponds to, and indicates, the approximate bottom center of basin 33. Drape 17 is disposed on cabinet 31 such that portions of the drape surrounding stand 2 are pushed down into, and conform to, basin 33 to form a drape receptacle with stand 2 positioned at the approximate center of the basin floor. The dimensions of frame 3 are greater than the dimensions of heater 60 (FIG. 3) such that the bottom edges of the frame rest on the basin floor coincident non-heated portions of the basin (i.e., beyond the perimeter of the heating element) as described above. Remaining portions of the drape cover top surface 34 and hang down the sides of cabinet 31. The drape receptacle typically contains liquid heated by the heating element disposed beneath basin 33 as described above. Stand 2 receives and supports objects disposed in the liquid filled basin above heated portions of the basin floor coincident the heater to prevent air from becoming trapped between an object base and the drape while maintaining the liquid and drape in thermal relation in substantially the same manner described above such that the drape absorbs the appropriate amount of thermal energy from the basin and does not puncture. Further, stand 2 separates the objects from vulnerable heated portions of the drape to prevent the drape from puncturing in substantially the same manner described above.

Operation of the drape and stand when disposed in a thermal treatment system basin containing heated liquid is now described with reference to FIG. 10. Specifically, drape 17 is disposed over cabinet 31 and within basin 33 to form a drape receptacle as described above. Stand 2 is substantially similar to any of the stands described above and is disposed at the basin floor either as part of the drape, or as a separate unit disposed in the basin above the drape. Objects, such as a graduator 14 containing an antibiotic solution or a surgical instrument 18, for example, are disposed in basin 33 on the top surface of platform 5 whereby the platform receives and supports the objects above heated portions of the basin floor coincident heating element 60. The space between the objects and the basin floor prevents air from becoming trapped between the object base and drape while maintaining thermal relation between the liquid and drape in substantially the same manner described above for the respective stand embodiments. Stand 2 ensures that the drape absorbs the proper amount of thermal energy from basin 33 while separating the objects from vulnerable heated portions of the drape, thereby preventing the drape from puncturing as described above.

It will be appreciated that the embodiments described above and illustrated in the drawings represent only a few of the many ways of implementing a surgical drape and elevated platform for use in heated thermal treatment system basins.

The stand may be constructed of high density polyethylene, ABS thermoplastic, propylene material or any material capable of withstanding temperatures of at least one hundred sixty degrees Fahrenheit, and sufficiently rigid to hold objects placed in the basin. The frame or platform of the stands may be any shape capable of fitting within a basin and having supports resting beyond the perimeters of a heater disposed adjacent the basin. The stand may be disposed on any part of the drape capable of being disposed in the basin and may be attached to the drape via ultrasonic energy, heat welding, solvents, adhesives, RF welding techniques or any other attachment process. The stand may be any device capable of elevating objects above the basin floor while resting on drape portions coincident non-heated portions of the basin. Further, stands may be disposed in the basins underneath the drape to prevent the drape from puncturing in substantially the same manner described above. The holes in the platforms may be of any size or shape and arranged in any fashion capable of maintaining the stand in a submerged state within a liquid filled basin and allowing thermal energy from the basin to heat the liquid. The curved longitudinal ends of the rectangular platform may be curved or bent in any fashion capable of elevating the platform above the basin floor. The longitudinal and transverse rods of the rectangular platform may be of any shape and arranged in any pattern to form a surface to support objects and maintain a submerged state in a liquid filled basin while allowing thermal energy from the basin to heat the liquid. Further, the spokes and rings or the longitudinal and transverse bars may be implemented by bars or rods having any cross-sectional shape and arranged in any pattern to form a surface having openings to support objects and maintain the stand in a submerged state in a liquid filled basin while allowing thermal energy from the basin to pass through the surface and heat the liquid. Any number of legs, type of frames, or other elevation mechanisms may be used to elevate the stand platforms. The entire stand may be molded as a single piece to minimize cost of manufacture.

The principles of the present invention are not limited to thermal treatment systems including a single basin, but are equally applicable to thermal treatment systems having a plurality of basins with each basin either warming or cooling a sterile liquid. Specifically, a thermal treatment system may include a plurality of basins disposed on a top surface for either cooling or warming a sterile liquid. The stands of the present invention may only be disposed in those basins warming the liquid in substantially the same manner as described above. The stands elevate objects above respective basin floors to prevent air from becoming trapped between the object base and the drape while maintaining thermal relation between the liquid and drape such that the drape absorbs the proper amount of thermal energy and does not puncture as described above. Further, the stands separate the objects from vulnerable heated portions of the drape to prevent the drape from puncturing as described above. Alternatively, drapes for a plural basin system may include a plurality of stands disposed on the drape corresponding to the approximate centers of basins warming the liquid. The stands may further function as indicators designating which portions of the drape are to be disposed in the warming basins. The drape is disposed over the plural basin system such that portions of the drape are disposed in all basins to form drape receptacles with the stands disposed at the bottom of only those basins warming the sterile liquid. The stands elevate objects disposed in the warming basins above the respective basin floors to prevent air from becoming trapped between the object base and drape while maintaining thermal relation between the liquid and drape such that the drape absorbs the proper amount of thermal energy and does not puncture as described above. Further, the stands separate the objects from vulnerable heated portions of the drape to prevent the drape from puncturing as described above.

From the foregoing description it will be appreciated that the invention makes available a novel surgical drape and stand for use in heated thermal treatment system basins wherein a stand is disposed in a thermal treatment system basin heating a sterile medium to elevate objects disposed in, and warmed by, the liquid above the basin floor to prevent the drape from puncturing. The stand may be either a separate unit disposed in the basin above the drape, or an integral part of the drape disposed in the basin when the drape is placed on the system.

Having described preferred embodiments of the new and improved surgical drape and stand for use in heated thermal treatment system basins, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. In a thermal treatment system having a basin including first and second basin portions and recessed in a system top surface with a heater disposed coincident only said first basin portions to heat a sterile medium contained within said basin, an apparatus to contain said sterile medium and objects within said basin, wherein said objects disposed in said basin are thermally treated by said heated sterile medium, said apparatus comprising:

a sterile drape for covering and hanging down from said top surface and being disposed within, and conforming to, said basin to form a drape receptacle to contain said sterile medium and objects in a sterile manner; and object support means disposed in said sterile medium within said drape receptacle for preserving sterility of said drape receptacle by preventing air from becoming trapped between said objects and said basin and overheating and puncturing portions of said drape disposed below said objects, said object support means including a support frictionally engaged to said drape at drape locations coincident said second basin portions to support said objects above a basin floor.

2. The apparatus of claim 1 wherein said support includes:

a platform for supporting said objects; and elevation means for elevating said platform above the basin floor, wherein said elevation means includes a plurality of spaced legs extending downwardly from said platform.

3. The apparatus of claim 2 wherein said elevation means is circular having circumferential edges and said platform includes:

a plurality of spokes extending from said circumferential edges of said elevation means toward the center of the elevation means; and a plurality of concentric rings extending radially outward from the center of the elevation means and reinforcing said spokes to strengthen said platform such that said platform supports said objects.

4. The apparatus of claim 2 wherein said elevation means is rectangular and said platform includes:

a plurality of longitudinal rods extending along longitudinal axes of said elevation means;

a plurality of transverse rods extending along transverse axes of said elevation means;

wherein said longitudinal and transverse rods are substantially perpendicular to each other and intersect to form a grid upon which said objects are supported.

5. The apparatus of claim 2 wherein:

said platform is circular having circumferential edges and a plurality of openings defined in said platform; and said plurality of spaced legs extend downwardly from said circumferential edges of said platform for elevating said platform above the basin floor.

6. The apparatus of claim 2 wherein:

said platform is rectangular having longitudinal ends and a plurality of openings defined in said platform; and said elevation means includes said longitudinal ends of said platform each curved downwardly from said platform to form said spaced leas and elevate said platform above the basin floor.

7. A surgical drape for use in a thermal treatment system having a basin recessed in a system top surface with a heater disposed beneath a basin floor to heat a sterile medium contained within said basin, wherein objects disposed in said basin are thermally treated by said heated sterile medium, said drape comprising:

a drape portion for covering and hanging down from said top surface and being disposed within, and conforming to, said basin to form a drape receptacle to contain said sterile medium; and a support disposed on said drape portion within said drape receptacle for supporting said objects above the basin floor to protect portions of said drape coincident said heater from overheating;

wherein said support is integral with said drape and disposed on said drape concentrically within the basin and indicates which portions of said drape are disposed within said basin.

8. The apparatus of claim 1 wherein:

said thermal treatment system includes a plurality of basins recessed in said top surface wherein a portion of said basins include heaters to heat said sterile medium;

said drape is disposed within each of said basins to form drape receptacles in respective basins to contain said sterile medium; and said apparatus further includes a plurality of said object support means having supports disposed within said drape receptacles corresponding to only those basins heating said sterile medium to support objects disposed in said heated basins above respective basin floors to prevent air from becoming trapped between said objects and said heated basins and overheating and puncturing portions of said drape disposed below said objects.

9. In a thermal treatment system having a basin including first and second basin portions and recessed in a system top surface with a heater disposed coincident only said first basin portions to heat a sterile medium contained within the basin, and a sterile drape covering and hanging down from the top surface and being disposed within the basin to form a drape receptacle to contain said sterile medium in a sterile manner, wherein objects disposed in the basin are thermally treated by said heated sterile medium, a support for placement within the basin comprising:

a platform for receiving and supporting the objects within the basin; and elevation means for placement in said sterile medium within said drape receptacle for preserving sterility of said drape receptacle by elevating said platform above a basin floor and preventing air from becoming trapped between the objects and the basin and overheating and puncturing portions of said drape disposed below said objects, wherein said elevation means frictionally engages said drape at drape locations coincident said second basin portions.

10. The support of claim 9 wherein the heated basin is rectangular or circular and said elevation means is rectangular or circular to match the basin in which the support is disposed.

11. The support of claim 9 wherein said elevation means is circular having circumferential edges and said platform includes:

a plurality of spokes extending from said circumferential edges of said elevation means toward the center of the elevation means; and a plurality of concentric rings extending radially outward from the center of the elevation means and reinforcing said spokes to strengthen said platform such that said platform supports said objects.

12. The support of claim 9 wherein said elevation means is rectangular and said platform includes:

a plurality of longitudinal rods extending along longitudinal axes of said elevation means;

a plurality of transverse rods extending along transverse axes of said elevation means;

wherein said longitudinal and transverse rods are substantially perpendicular to each other and intersect to form a grid upon which said objects are supported.

13. The support of claim 9 wherein:

said platform is circular having circumferential edges and a plurality of openings defined in said platform; and said elevation means includes a plurality of legs extending downwardly from said circumferential edges of said platform for elevating said platform above the basin floor.

14. The support of claim 9 wherein:

said platform is rectangular having longitudinal ends and a plurality of openings defined in said platform; and said elevation means includes said longitudinal ends of said platform curved downwardly from said platform to elevate said platform above the basin floor.

15. In a thermal treatment system having a basin including first and second basin portions and recessed in a system top surface with a heater disposed coincident only said first basin portions to heat a sterile medium contained within the basin, wherein objects disposed in the basin are thermally treated by said heated sterile medium, a method for supporting said objects in the basin comprising the steps of:

(a) placing a sterile drape over the system top surface such that the drape covers and hangs down from the top surface and is disposed within said basin to form a drape receptacle to contain said sterile medium in a sterile manner;

(b) disposing a support in said sterile medium within said drape receptacle to receive said objects, wherein said support frictionally engages said drape at drape locations coincident said second basin portions; and (c) preserving sterility of said drape receptacle and preventing air from becoming trapped between said objects and said basin and overheating and puncturing portions of said drape disposed below said objects by supporting said objects above a basin floor via the support.

16. In a thermal treatment system having a basin recessed in a system too surface with a heater disposed beneath a basin floor to heat a sterile medium contained within the basin, wherein objects disposed in the basin are thermally treated by said heated sterile medium, a method for supporting said objects in the basin comprising the steps of:

(a) placing a drape over the system top surface such that the drape covers and hangs down from the top surface and is disposed within said basin to form a drape receptacle to contain said sterile medium; and (b) disposing a support within said drape receptacle for supporting said objects above the basin floor to protect portions of said drape coincident said heater from overheating and puncturing, wherein step (b) further includes the step of:

(b.1) forming said drape and support as an integral unit.

17. The method of claim 15 wherein step (b) further includes:

(b.1) forming said support to include a platform for supporting said objects, and elevation means for elevating said platform above the basin floor.

18. The method of claim 17 wherein step (b.1) further includes:
(b.1.1) forming said support such that said elevation means is circular having circumferential edges and said platform includes a plurality of spokes extending from said circumferential edges of said elevation means toward the center of said elevation means, and a plurality of concentric rings extending radially outward from the center of the elevation means and reinforcing said spokes to strengthen said platform such that said platform supports said objects.

19. The method of claim 17 wherein step (b.1) further includes:
(b.1.1) forming said support such that said elevation means is rectangular and said platform includes a plurality of longitudinal rods extending along longitudinal axes of said elevation means, and a plurality of transverse rods extending along transverse axes of said elevation means, wherein said longitudinal and transverse rods are substantially perpendicular to each other and intersect to form a grid upon which said objects are supported.

20. The method of claim 17 wherein step (b.1) further includes:
(b.1.1) forming said support such that said platform is circular having circumferential edges and a plurality of openings defined in said platform, and said elevation means includes a plurality of legs extending downwardly from said circumferential edges of said platform for elevating said platform above the basin floor.

21. The method of claim 17 wherein step (b.1) further includes:
(b.1.1) forming said support such that said platform is rectangular having longitudinal ends and a plurality of openings defined in said platform, and said elevation means includes said longitudinal ends of said platform curved downwardly from said platform to elevate the platform above the basin floor.

22. The method of claim 16 wherein step (b.1) further includes:
(b.1.1) forming said drape and support as an integral unit such that said support corresponds to the center of the basin and indicates which portions of said drape are disposed within said basin.

23. The method of claim 15 wherein said thermal treatment system includes a plurality of basins recessed in said top surface wherein a portion of said basins include heaters to heat said sterile medium, and step (a) further includes:
(a.1) placing said drape over the system top surface such that said drape is disposed within each of said basins to form drape receptacles in respective basins to contain said sterile medium;
step (b) further includes:
(b.1) disposing supports within said drape receptacles associated with those basins heating said sterile medium; and
step (c) further includes:
(c.1) preventing air from becoming trapped between said objects and said basins and overheating and puncturing portions of said drape disposed below said objects by supporting said objects disposed in said heated basins above respective basin floors.

24. In a thermal treatment system having a basin including first and second basin portions and recessed in a system top surface with a heater disposed coincident only said first basin portions to heat a sterile medium contained within the basin and a sterile drape placed over the system top surface to cover and hang down from the top surface and be disposed within said basin to form a drape receptacle to contain said sterile medium in a sterile manner, wherein objects disposed in the basin are thermally treated by said heated sterile medium, a method for supporting said objects in the basin comprising the step of:
(a) forming a support for placement within the basin including a platform for receiving and supporting the objects and elevation means for placement in said sterile medium within said drape receptacle for preserving sterility of said drape receptacle by elevating the platform above a basin floor and preventing air from becoming trapped between the objects and the basin and overheating and puncturing portions of said drape disposed below said objects, wherein said elevation means frictionally engages said drape at drape locations coincident said second basin portions.

25. In a thermal treatment system having a basin recessed in a system top surface with a heater disposed beneath a basin floor to heat a sterile medium contained within the basin and a drape placed over the system top surface to cover and hang down from the top surface and be disposed within said basin to form a drape receptacle to contain said sterile medium, wherein objects disposed in the basin are thermally treated by said heated sterile medium, a method for supporting said objects in the basin comprising the step of:
(a) forming a support for placement within the basin including a platform for receiving and supporting the objects and elevation means for elevating the platform above the heated basin floor and preventing air from becoming trapped between the objects and the basin and overheating portions of said drape disposed below said objects, wherein step (a) further includes:
(a.1) forming said support and drape as an integral unit.

26. In a thermal treatment system having a basin including first and second basin portions and recessed in a system top surface with a heater disposed coincident only said first basin portions to heat a sterile medium contained within the basin and a sterile drape placed over the system top surface to cover and hang down from the top surface and be disposed within said basin to form a drape receptacle to contain said sterile medium in a sterile manner, wherein objects disposed in the basin are thermally treated by said heated sterile medium, a method of protecting the drape from puncturing comprising the step of:
(a) preserving sterility of said drape receptacle by preventing air from becoming trapped between the objects and the basin and overheating and puncturing portions of said drape disposed below said objects by supporting the objects within the basin above a basin floor via a support disposed in said sterile medium within the drape receptacle and frictionally engaged to said drape at drape locations coincident said second basin portions.

27. The apparatus of claim 1 wherein said support is frictionally engaged to said drape at drape locations positioned beyond the confines of said heater.

28. The support of claim 9 wherein said elevation means frictionally engages said drape at drape locations positioned beyond the confines of said heater.

29. The method of claim 15 wherein step (b) further includes:
(b.1) disposing said support in said sterile medium within said drape receptacle wherein said support frictionally engages said drape at drape locations positioned beyond the confines of said heater.

30. The method of claim 24 wherein step (a) further includes:
   (a.1) forming said support to include said elevation means frictionally engaged to said drape at drape locations positioned beyond the confines of said heater.

31. The method of claim 26 wherein step (a) further includes:
   (a.1) preserving sterility of said drape receptacle by supporting the objects within the basin above the basin floor via said support frictionally engaged to said drape at drape locations positioned beyond the confines of said heater.

* * * * *